United States Patent [19]

Prevorsek et al.

[11] 3,969,930
[45] July 20, 1976

[54] TESTING VISCOELASTIC SOLIDS

[75] Inventors: Dusan Ciril Prevorsek; Young Doo Kwon; Raj Kumar Sharma, all of Morristown; Edward T. Gilliam, Lake Hiawatha, all of N.J.

[73] Assignee: Allied Chemical Corporation, Morris Township, N.J.

[22] Filed: Apr. 10, 1975

[21] Appl. No.: 567,144

[52] U.S. Cl. .................................................. 73/91
[51] Int. Cl.² ......................................... G01N 3/34
[58] Field of Search ................. 73/91, 100, 15.6, 95

[56] References Cited
UNITED STATES PATENTS

| | | | |
|---|---|---|---|
| 1,558,594 | 10/1925 | Coffin | 73/95 X |
| 2,916,912 | 12/1959 | Gibson | 73/91 |
| 3,214,969 | 11/1965 | Swanson | 73/91 |
| 3,826,902 | 7/1974 | Claxton et al. | 73/95 X |

*Primary Examiner*—Jerry W. Myracle
*Attorney, Agent, or Firm*—John P. Kirby, Jr.

[57] ABSTRACT

An apparatus and method for testing viscoelastic solids, such as tire cord. The apparatus includes: a holding means, a pretension means, a displacement generator, and a mechanical-electrical transforming means. The holding means holds the material in a predetermined position. The pretension means applies tension during testing. The displacement generator has an eccentric means for applying cyclic displacement. The mechanical-electrical transforming means transforms mechanical motion into electrical signals, such as a stress signal, a strain signal and a differentiated strain signal. There is a phase lag between the stress signal and the strain signal and the phase lag may vary in amount and direction as a function of time. The apparatus may also include: an integrating means for integration of a stress-strain hysteresis loop; and a display means for displaying an output of the integrating means to measure the area of the hysteresis loop and thereby determine energy loss. The method includes: applying strain to the material, with resulting stress developed in the material; transforming the strain into an electrical strain signal having a strain wave form; transforming the resulting stress into an electrical stress signal having a stress wave form; controlling the strain to produce a substantially sinusoidal strain wave form representing strain; and allowing the stress to produce a stress wave form representing stress which may be non-sinusoidal or sinusoidal.

26 Claims, 15 Drawing Figures

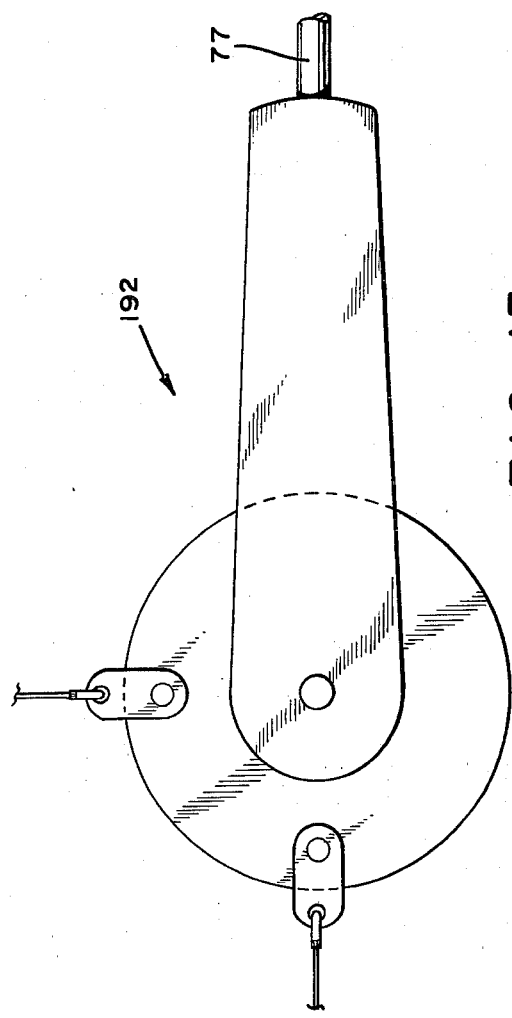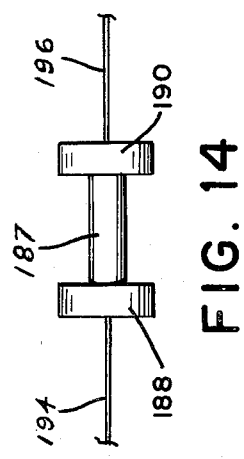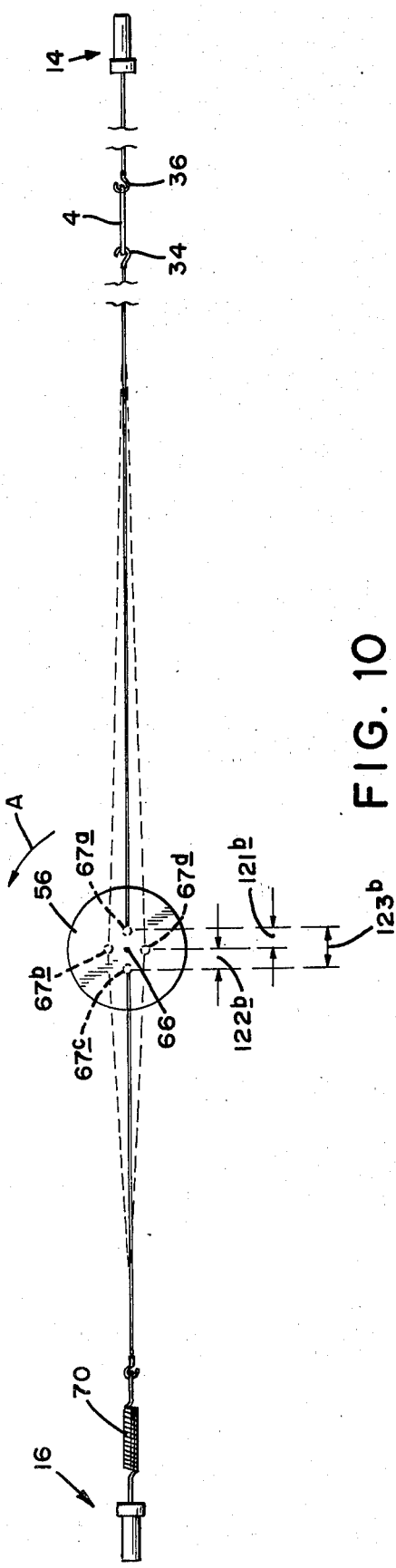

TESTING VISCOELASTIC SOLIDS

BACKGROUND OF THE INVENTION

The invention relates to an apparatus and method for testing and measuring viscoelastic solids, including their ability to withstand stress and strain. An example of a use for the invention is to test tire cord used for reinforcing pneumatic tires.

An earlier design of an apparatus related to the present invention is disclosed in U.S. Pat. No. 3,893,331 filed Apr. 26, 1973 and entitled "Method and Apparatus for Determining Side Wall Temperature in Running Tires". U.S. Pat. application Ser. No.. 528,610 filed Dec. 2, 1974 now U.S. Pat. No. 3,934,452 and entitled "Method of Determining Dynamic Strain in Composite Structures" discloses that viscoelastic properties, moduli $E'$ and $E''$ and tan $\delta$ vary cyclically during the cyclic straining of cords. Toyo Measuring Instruments Co., Ltd. of Tokyo, Japan manufactures an apparatus known as a "Direct Reading Dynamic Viscoelastometer" and by the name "VIBRON" which differs in structure and operation from the present invention. Conventional linear viscoelastic theory is disclosed in "Viscoelastic Properties of Polymers," by John D. Ferry, published by John Wiley & Sons, Inc., 1970, particularly pages 12 and 606–609. Other testing apparatus are disclosed in U.S. Pat. No. 1,558,594 to Coffin and in the Journal of Applied Physics, Vol. 18, June 1947, page 586; Vol. 17, August 1946, page 699; and Vol. 16, July 1945, page 398.

SUMMARY OF THE INVENTION

The apparatus and method of the present invention is adapted for testing a viscoelastic material. The apparatus includes: a holding means, a pretension means, a displacement generator, and a mechanical-electrical transforming means. The holding means is connected to the material for holding the material in a predetermined position during testing. The pretension means is coupled to the material for applying tension to the material during testing. The displacement generator has an eccentric means coupled to the material for applying cyclic displacement to the material. The mechanical-electrical transforming means is coupled to the material for transforming mechanical motion into electrical signals.

The mechanical-electrical transforming means includes: a first force transforming means, preferably a second force transforming means, and, preferably a third force transforming means. The first force transforming means transforms mechanical stress developed in the material into an electrical stress signal. The second force transforming means transforms mechanical strain applied to the material into an electrical strain signal. The third force transforming means is arranged at an angle of 90° with reference to the first force transforming means and with reference to the second force transforming means. The third force transforming means is a mechanical differentiating means which transforms a time derivative of mechanical strain applied to the material into an electrical cosine signal. The strain signal has at least a substantially sinusoidal wave form. The stress signal may have a non-sinusoidal or a sinusoidal wave form.

There is a phase lag between the stress signal and the strain signal and the phase lag may vary in amount and direction as a function of time. Where the phase lag varies in amount and direction the stress signal lags in time behind the strain signal during expansion of the material and the strain signal lags in time behind the stress signal during contraction of the material. The apparatus may also include: an integrating means for integration of a stress-strain hysteresis loop; and a display means for displaying an output of the integrating means to measure the area of the hysteresis loop and thereby determine energy loss.

The method includes the following steps: applying strain to the material, with resulting stress also being applied to the material when such strain is developed in the material; transforming the strain applied to the material into an electrical strain signal having a strain wave form and an amplitude; transforming the resulting stress into an electrical stress signal having a stress wave form and an amplitude; controlling the strain applied to the material to produce at least a substantially sinusoidal strain wave form representing strain and preferably a strain wave form which is as precisely sinusoidal as possible; and allowing the stress applied to the material to produce a stress wave form representing stress which may be non-sinusoidal or which may be sinusoidal. The method further includes observing that there is a phase lag between the strain wave form and the stress wave form and that the phase lag varies in amount and sometimes in direction, depending upon the characteristics of the material.

The step of observing that the phase lag varies in amount and sometimes in direction includes: displaying the strain wave form and the stress wave form as a function of time on the same scale; and arranging the amplitudes of the strain wave form and the stress wave form to be equal. The method further includes: displaying the stress wave form along a vertical axis; displaying the strain wave form along a horizontal axis; observing a formation of a hysteresis loop; and determining the area within the hysteresis loop. The area within the hysteresis loop reflects the energy loss in the material 4. The step of measuring the area within the hysteresis loop may include: using an integrating means to measure such area. The step of using an integrating means includes: transforming the strain applied to the material into a differentiated strain signal; and integrating the differentiated strain signal and the stress signal. The step of transforming the strain applied to the material into a differentiated strain signal includes: differentiating the strain mechanically by an arrangement of a differentiating mounting means at an angle of 90° in reference to a strain mounting means.

The method also includes a procedure for aligning and preparing the apparatus for use.

DESCRIPTION OF THE DRAWINGS

FIG. 2 shows the pretension means.

FIG. 3 shows an eccentric mechanical means and a first embodiment of a stress mounting means.

FIG. 7 shows an eccentric head and slide.

FIG. 9 shows a temperature chamber.

FIG. 10 is a simplified illustration of a portion of FIG. 1. FIG. 10 shows the eccentric displacement means.

FIG. 11 shows a mounting means for a third force transforming device.

FIG. 14 is a simplified illustration of a fourth embodiment of a holding means used for testing and measuring a material's ability to withstand compression.

FIG. 15 is a simplified illustration of a second embodiment of a stress mounting means.

DETAILED DESCRIPTION

General Orientation

Figure 1:
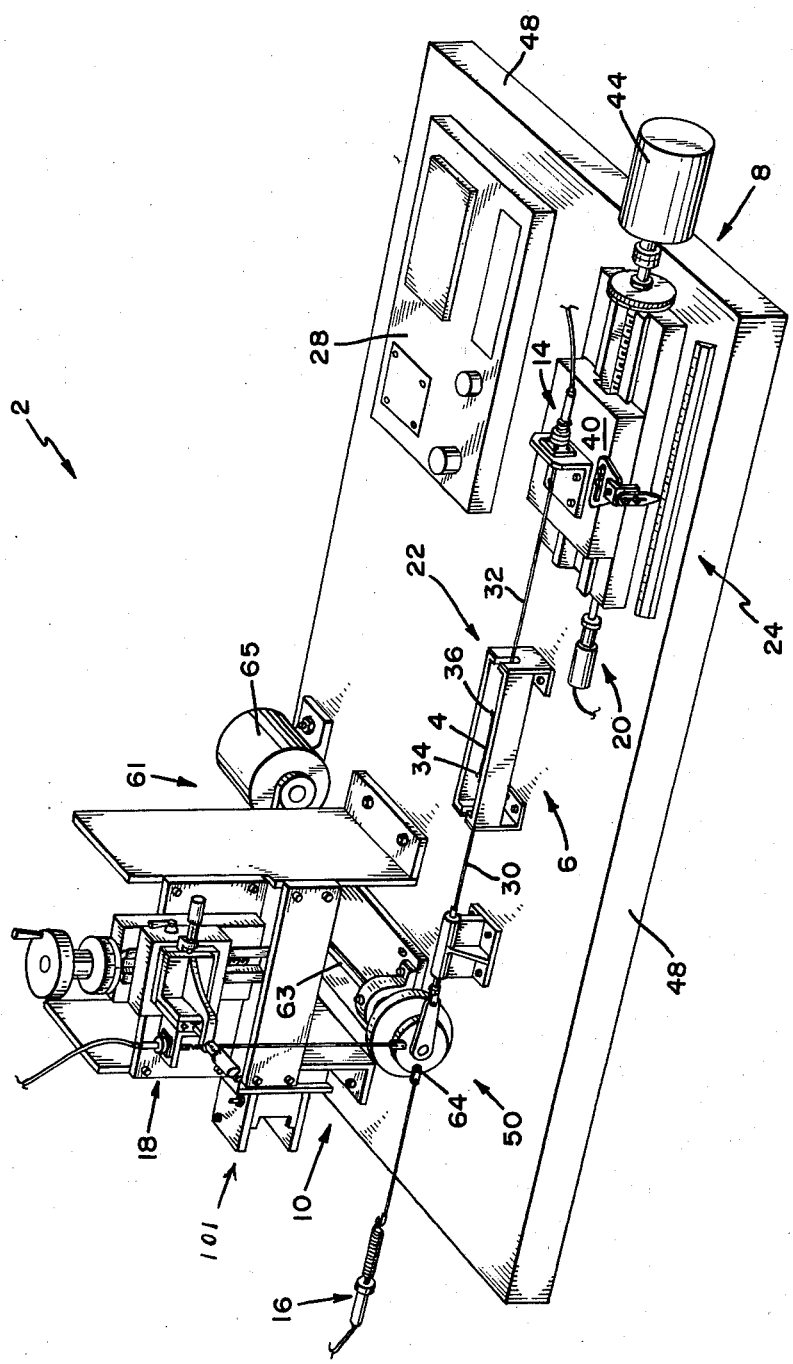
FIG. 1 is an isometric view of major portions of the apparatus of the present invention, including a first embodiment of a holding means.

Referring to FIG. 1, the apparatus of the present invention, referred to generally by the numeral 2, is adapted for testing a viscoelastic solid material. A viscoelastic material is a material possessing viscous properties and elastic properties. For example, the material may be a strand of monofilament or multifilament material. The multifilament or polyfilament material may, for example, be a specimen of tire cord made of a polymeric fiber and used for reinforcing pneumatic tires. The material to be tested may also be a yarn, film, rod or solid block of material. In the primary embodiment, illustrated in FIGS. 1-11, the material 4 is a multifilament tire cord which may be tested under conditions which simulate conditions existing when a tire containing such tire cord is running on a vehicle, such as an automobile or truck. The material 4 is tested to determine and measure selected physical-structural properties of the material 4, including its ability in the presence of heat to withstand stress, strain, and physical-structural fatigue. The apparatus 2 is specially adapted to reflect the effect of a phase lag between stress applied to the material 4 and strain applied to the material 4.

The apparatus 2 includes the following major components: a holding means 6; a pretension means 8; a sinusoidal displacement generator 10; and a mechanical-electrical transforming means. The mechanical-electrical transforming means is indirectly coupled to the material 4 and is adapted for transforming mechanical motion in the material 4 into electrical signals. The mechanical-electrical transforming means includes: a first force transforming means 14; and a second force transforming means 16. Preferably, the mechanical-electrical transforming means also includes: a third force transforming means 18 and a position transforming means 20. Preferably, the apparatus 2 also includes: a temperature chamber 22; a permanent elongation means 24; and an integrating means 28.

Prior to testing, the viscoelastic material 4 is formed into a shape suitable for mounting in the holding means 6. For example, the material 4 may be formed into a closed loop. The closed loop may be achieved by using a length of material 4 which preferably is in the range between 4 inches and 16 inches. The material 4 has two loose ends which are tied together by a knot. The closed loop has a length which is approximately one-half of the length of material 4 before the knot is tied in the material 4. Preferably, the closed loop has a length in the range between 2 inches and 8 inches. The holding means 6 is connected to the closed loop of material 4 and is adapted for holding the material 4 in a predetermined position during testing, preferably in a horizontal plane.

Holding Means

Referring to FIG. 1, for purposes of testing for stress and strain the holding means 6 includes two substantially rigid structural members, preferably two lengths of stiff wire, an active wire 30 and a passive wire 32. Both the active wire 30 and the passive wire 32 have two ends. One end of the active wire 30, the end adjacent to the material 4, has an engaging means, such as a hook 34, for engaging the material 4. Likewise, one end of the passive wire 32, the end adjacent to the material 4, also has an engaging means, such as a hook 36, for engaging and holding the material 4. The other end of the active wire 30 is connected to the displacement generator 10. The other end of the passive wire 32 is connected to the pretension means 8. The knot in the loop of the viscoelastic material 4 is preferably arranged either at the hook 34 of the active wire 30 or at the hook 36 of passive wire 32 to avoid or at least minimize loosening, untying or elongation in the knot during testing and to avoid testing variation between the length of the loop which does have the knot and the length of the loop which does not have the knot. The active wire 30 and the passive wire 32 should have negligible weight. The active wire 30 and the passive wire 32 should also have a negligible amount of twist in order to avoid variations in their length during testing. Preferably, a rigid, monofilament metal wire, such as piano wire, is used for the active wire 30 and the passive wire 32. Thus, one end of the material 4 is indirectly coupled to the pretension means 8 by means of the passive wire 32. The opposite end of the material 4 is indirectly coupled to the displacement generator 10 by means of active wire 30. No sensors, such as transducers, need be implanted in the material 4 being tested.

Pretension Means

Figure 2:
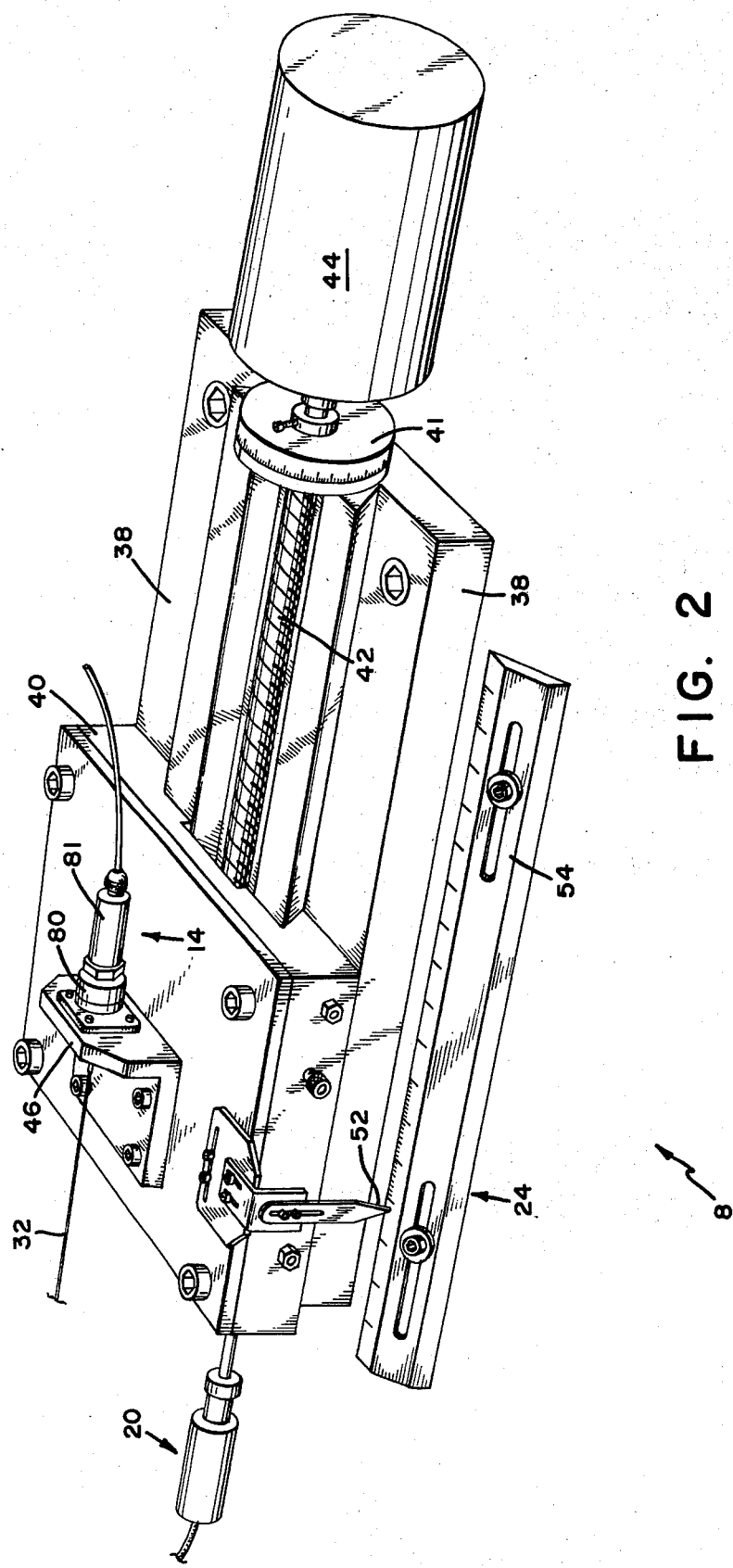
FIG. 2 is an isometric view of a portion of FIG. 1.

Referring to FIG. 2, the pretension means 8 is adapted for applying tension to the passive wire 32 and indirectly to the material 4 during testing. The pretension means 8 includes: a stationary member 38; a movable member 40; a lead screw 42; and a servo motor 44. The end of the passive wire 32 which is opposite from the material 4 is connected to the first force transforming means 14 which is mounted by means of an L-shaped bracket 46 on the movable member 40. Referring to FIG. 1, the stationary member 38 is mounted on a platform 48. The movable member 40 is mounted on the stationary member 38. The lead screw 42 is arranged between the movable member 40 and the stationary member 38. One end of the lead screw 42 is connected to the movable member 40 and the other end of the lead screw 42 is connected to servo motor 44. The lead screw 42 has screw threads which engage screw threads on a channel in the top of the stationary member 38 and screw threads in a channel on the bottom of movable member 40. The pre-tension means 8 applies a selected amount of tension, preferably constant tension, to the material 4 by means of the lead screw 42 and the servo motor 44. Gradually, the servo motor 44 rotates the lead screw 42 in a direction so as to draw the movable member 40 toward the servo motor 44. As a result, the movable member 40 moves with reference to the stationary member 38 toward the servo motor 44 during testing of the material 4. Such movement of the movable member 40 compensates for transitory or permanent elongation or contraction in the material 4 during testing and provides a constant tension on the material 4.

The permanent elongation means 24 determines the permanent elongation occurring in the material 4 during testing. Permanent elongation is sometimes referred to as "creep". The permanent elongation means 24 includes a pointer 52 and a scale 54 which provide an approximate measurement of changes in length of the material 4. The pointer 52 is mounted on the movable member 40 of the pretension means 8. The scale 54 is mounted on the platform 48 adjacent to the stationary member 38 of the pretension means 8. In operation, the pointer 52 indicates the lengths of the material 4 before and after testing. The difference in lengths is the permanent elongation which occurred in the material 4 during testing.

The pretension means 8 also includes a graduated dial 41 on an end of the lead screw 42 adjacent to the servo motor 44. The graduated dial 41 indicates the amount of rotation of the lead screw 42 and the amount of movement of the movable member 40 during testing. The position transforming means 20 may be an electronic cell, such as a linear voltage differential transformer. The position transforming means 20 and the graduated dial 41 provide more accurate measurement of changes in length of the material 4, than the permanent elongation means 24, especially as to transitory changes.

Displacement Generator

Figure 3:
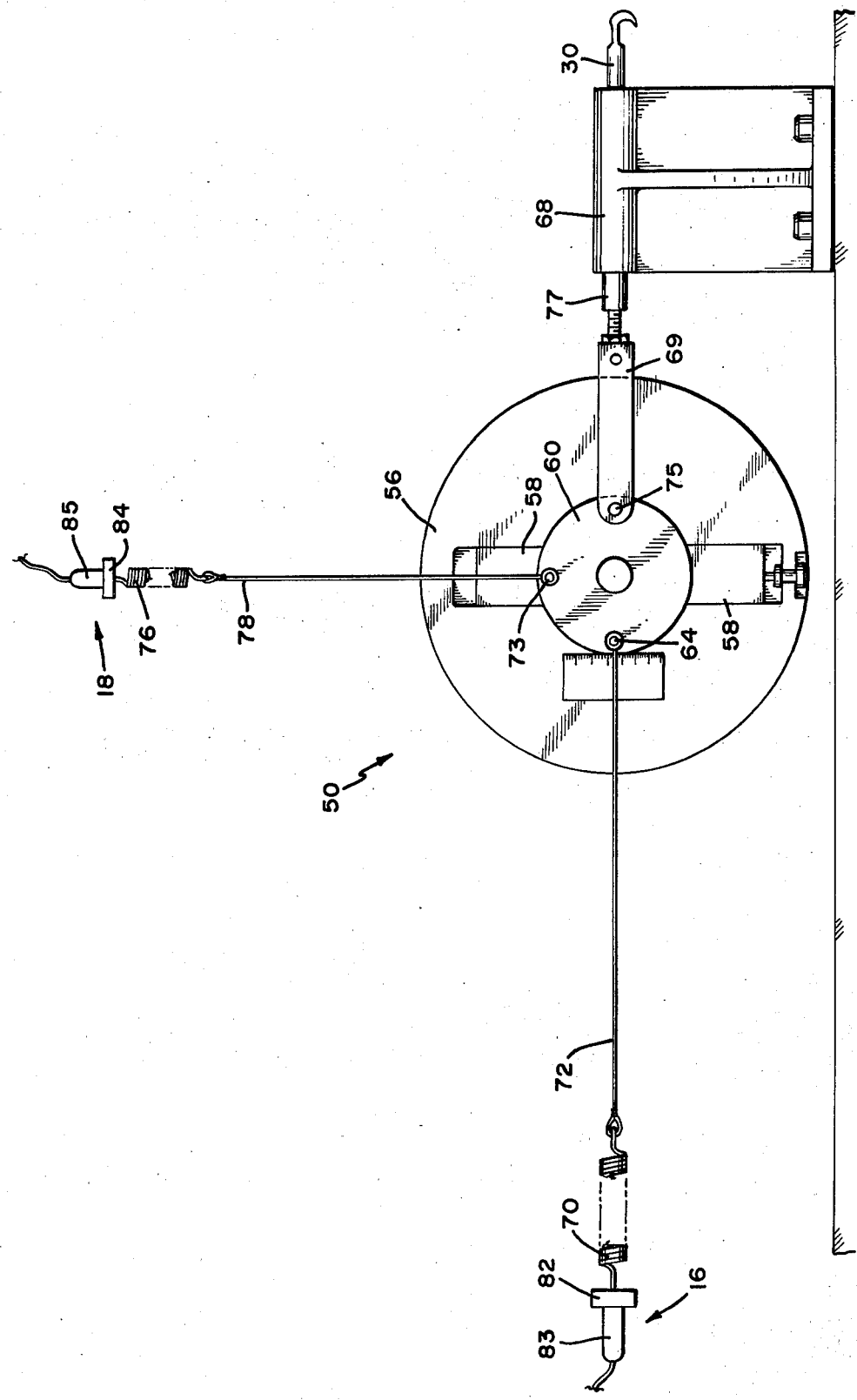
FIG. 3 is a frontal view of a portion of FIG. 1.

Referring to FIGS. 1 and 3, the displacement generator 10 has an eccentric means 50 indirectly coupled to the material 4 through the active wire 30. The displacement generator 10 is adapted for applying repetitive and cyclic, sinusoidal displacement as sinusoidal strain to the material 4. The displacement generator 10 controls the strain applied to the material 4 and allows the stress to vary. As a result, the viscoelastic material 4 undergoes at least substantially sinusoidal strain and preferably strain which is as precisely sinusoidal as possible. The material 4 also undergoes either non-sinusoidal or sinusoidal stress, as well as tension and physical - structural fatigue. The eccentric means 50 may preferably be mechanical, but may also be electromechanical. The eccentric means 50 of the displacement generator 10 includes: a concentric head 56; an eccentric slide 58; a centerpiece 60; and a drive means 61.

The drive means 61 provides a source of rotating power to the eccentric mechanical means 50. The drive means 61 includes a drive shaft 63, a drive motor 65, a speed reducer (not shown) and a speed control (not shown). The concentric head 56 is rotatable on the drive shaft 63 and is driven by the drive motor 65. The speed control allows control and variation of the speed of rotation of the drive motor 65, drive shaft 63 and concentric head 56 in order to simulate various speeds of rotation of a tire on a vehicle. The concentric head 56 has a center which is concentric with the drive shaft 63.

Figure 7:
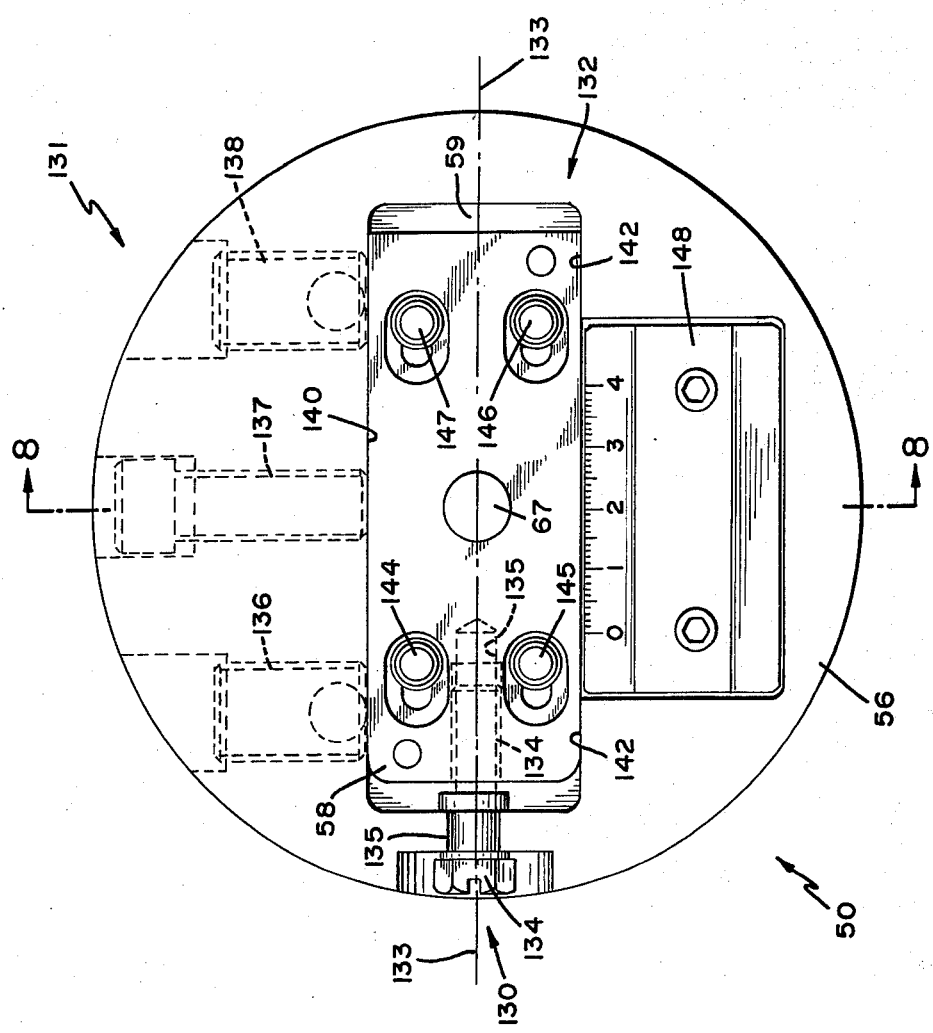
FIG. 7 is a front plan view of a portion of FIG. 3.
Figure 8:
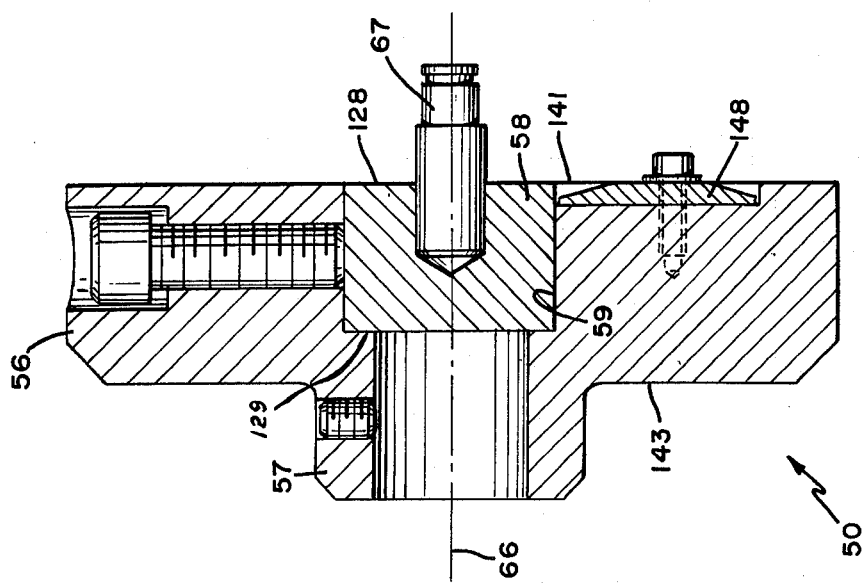
FIG. 8 is a vertical section along the lines 8—8 of FIG. 7.

Referring to FIGS. 7 and 8, preferably, the concentric head 56 is a heavy metal disc having a bushing 57 and set screw for mounting the concentric head 56 on an end of the drive shaft 63 adjacent to the concentric head 56. The eccentric slide 58 has a rectangular shape and is adpated to fit in a slot 59 of the concentric head 56. The slot 59 is located on the outer face of the concentric head 56 opposite from the face of the concentric head 56 on which the bushing 57 is located. The length of the slot 59 is approximately one percent to 20 percent longer than the length of the eccentric slide 58. The width of the slot 59 is slightly larger than the width of the eccentric slide 58 in order to provide sufficient tolerance so that the slide 58 can be moved in a direction parallel to the longitudinal axis of the slide 58 and the slot 59. The eccentric slide 58 has an eccentric shaft 67 which is movable with reference to the concentric head 56 for eccentric displacement of the eccentric shaft 67 with reference to the center of the concentric head 56.

Referring to FIGS. 3 and 8, the circular centerpiece 60 is mounted on the eccentric shaft 67 of the eccentric slide 58. The eccentric shaft 67 extends into a hole in the center of the centerpiece 60 and is rotatable with reference to the centerpiece 60. The eccentric shaft 67 transmits cyclic displacement to the material 4. The centerpiece 60 has a center which is concentric with the shaft 67 of the slide 58 and eccentrically displaced from the center of the concentric head 56.

The centerpiece 60 includes: a stress mounting means 75, a strain mounting means 64 and a differentiating mounting means 73, each of which are indirectly coupled to the material 4. One end of a stress arm 69 is rotatably mounted by the stress mounting means 75, such as a pivot point, on the outer periphery of the centerpiece 60. The opposite end of the stress arm 69 is indirectly coupled to the active wire 30 and the material 4 by means of a stress rod 77 which slideably passes through a first linear bearing 68. The strain mounting means 64, such as a pivot point, is rotatably mounted on the outer periphery of the centerpiece 60. The strain mounting means 64 is connected to a strain wire 72, which in turn is connected to a strain spring 70, which in turn is connected to the second force transforming means 16. The differentiating mounting means 73, such as a pivot point, is also rotatably mounted on the outer periphery of the centerpiece 60. The differentiating mounting means 73 is connected to a differentiating wire 78 which in turn is connected to a differentiating spring 76, which in turn is connected to the third force transforming means 18. The strain mounting means 64 and the differentiating mounting means 73 are both indirectly coupled to the material 4 by means of the stress arm 69, stress rod 77, and the active wire 30.

The stress mounting means 75 is arranged at an angle of 90 degrees with respect to the differentiating mounting means 73. The stress arm 69 is arranged colinearly with the strain wire 72, by arranging the stress mounting means 75 at an angle of approximately and preferably precisely 180 degrees with respect to the strain mounting means 64. The differentiating mounting means 73 is arranged at an angle of 90° with respect to the stress mounting means 75 and with respect to the strain mounting means 64. It is important that the first force transforming means 14, an extended centerpoint of the eccentric head 56 and the drive shaft 63, and the second force transforming means 16 be colinear. Likewise, it is important that the third force transforming means 18 be perpendicular to a line formed by the first force transforming means 14, the extended centerline of the concentric head 56 and the second force transforming means 16. This colinear arrangement provides advantages of design simplification and minimization of deflection error between the first force transforming means 14 and the second force transforming means 16.

Force Transforming Means

Referring to FIGS. 1 and 2, the first force transforming means 14 includes a first load cell 80 and a first electronic cell 81, such as a mechanical-electrical transducer. The first force transforming means 14 is mounted on the bracket 46 of the pretension means 8. The first force transforming means 14 is indirectly coupled to the material 4 through the passive wire 32 and transforms mechanical stress developed into the material 4 into an electrical stress signal. Referring to FIGS. 1 and 3, the second force transforming means 16 includes a second load cell 82 and a second electronic cell 83, such as a mechanical-electrical transducer. The second force transforming means 16 is indirectly coupled to the displacement generator 10 by means of the strain spring 70, the strain wire 72 and strain mounting means 64. The second force transforming means 16 is also indirectly coupled to the material 4 through the active wire 30 in order to transform mechanical strain applied to the material 4 into an electrical strain signal. The active wire 30 reflects strain. The passive wire 32 reflects stress.

Referring to FIGS. 1 and 3, the third force transforming means 18 includes a third load cell 84 and a third electronic cell 85, such as a mechanical-electrical transducer. The third force transforming means 18 is indirectly coupled to the displacement generator 10 by means of the differentiating spring 76 and the differentiating wire 78. The third force transforming means 18 generates an electrical differentiated strain signal which is a cosine wave signal corresponding to a mathematical differentiation of the strain signal from the second force transforming means 16. The mathematical differentiation is with respect to the angular position of the eccentric shaft 67 around the drive shaft 63. Thus, the mechanical arrangement of the differentiating mounting means 73 on the centerpiece 60 of the displacement generator 10 at an angle of 90 degrees with reference to the strain mounting means 64 in combination with the third force transforming means 18 constitutes a mechanical differentiation means which performs the function of differentiating the strain mechanically, rather than electronically. Such mechanical differentiation means eliminates the noise that would be produced by an electronic differentiation means.

Processing of Electronic Signals

Figure 4:
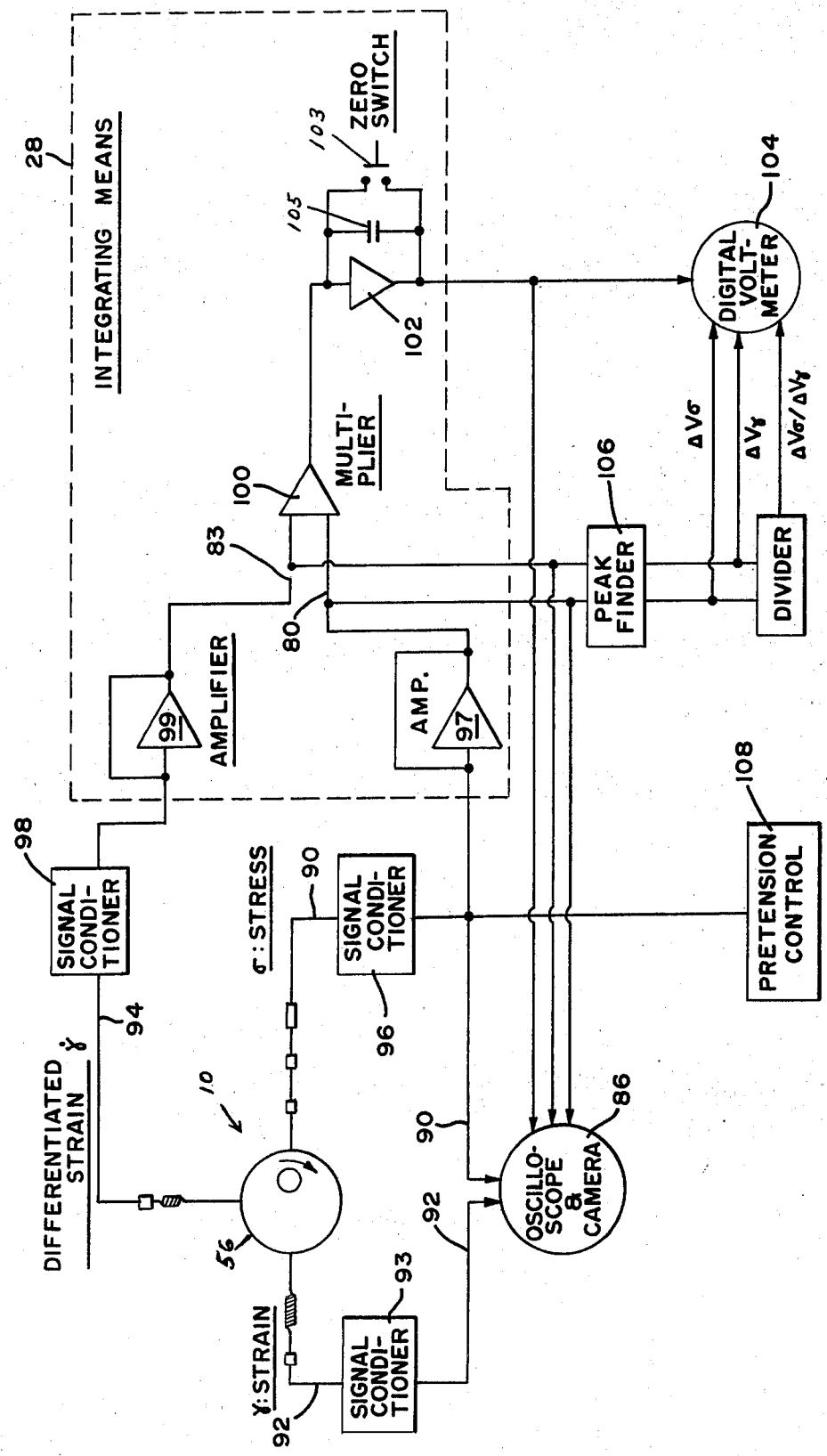
FIG. 4 is a schematic diagram of an electronic circuit for the apparatus shown in FIG. 1.

Referring to FIG. 4, the stress signal ($\sigma$) 90 from the first force transforming means 14; the strain signal ($\gamma$) 92 from the second force transforming means 16; and the differentiated strain signal ($\dot{\gamma}$) 94 from the third force transforming means 18 are processed in the following ways. The stress signal 90 is conducted to a first signal conditioner 96. The first signal conditioner 96 includes an amplifier and a power supply. The power supply supplies power to the first electronic cell 81 of the first force transforming means 14 for generation of the stress signal 90. The stress signal 90, as an output from the first signal conditioner 96, is conducted to a first amplifier 97 of an electronic integrator means 28.

The strain signal 92 is conducted to a second signal conditioner 93. The second signal conditioner 93 conditioner 93 includes an amplifier and a power supply. The power supply supplies power to the second electronic cell 83 of the second force transforming means 16 for generation of the strain signal 92. The strain signal 92, as an output from the second signal conditioner 93, is conducted to display means, such as an oscilloscope 86.

The differentiated strain signal 94 is conducted to a third signal conditioner 98. The third signal conditioner 98 includes an amplifier and a power supply. The power supply provides power to the third electronic cell 85 of the third force transforming means 18. As an output from the third signal conditioner 98, the differentiated strain signal 94 is conducted to a second amplifier 99 of the integrator means 28. The stress signal from the first amplifier 97 and the differentiated strain signal 94 from the second amplifier 99 are conducted to a multiplier 100 of the integrator means 28. The output from the multiplier 100 is conducted through an integrating amplifier 102 and then to a voltmeter 104, such as a digital voltmeter.

The stress signal 90 and/or the differentiated strain signal 94 are also conducted to a peak finder 106, which measures the peak to peak voltage of the stress signal 90 or the differentiated strain signal 94. The stress signal 90 as an output from the first signal conditioner 96, is also conducted to a pretension control 108, such as the servo motor 44 of the pretension means 8 (FIG. 1) to provide a constant tension on the material 4. Optionally, the same signal conditioner may be used for the strain signal 92 and the differentiated strain signal 94 by use of a switching means.

Display of Stress and Strain

Figure 5:
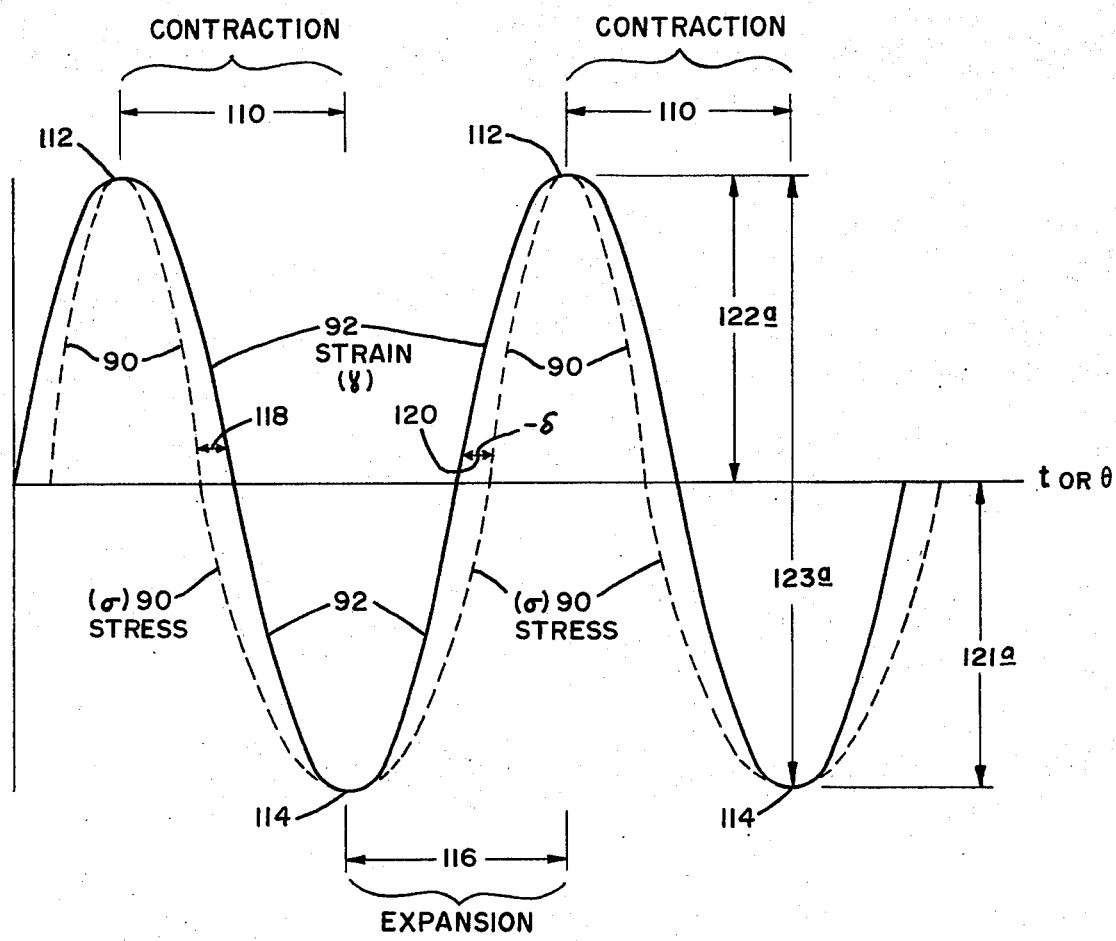
FIG. 5 is an illustration of a display of stress-strain variation, plotted with reference to time and angle.

Referring to FIGS. 4 and 5, the stress signal ($\sigma$) 90 as an output from the first signal conditioner 96 (FIG. 4) and the strain signal ($\gamma$) 92 as an output from the second signal conditioner 93 (FIG. 4) may be displayed on a display means, such as the oscilloscope 86. Both the stress signal ($\sigma$) 90 and the strain signal ($\gamma$) 92 are displayed along a vetical axis which is proportional to voltage. Time (t), which is proportionate to the angle ($\theta$) of cyclic strain, is displayed along the horizontal axis.

The voltage of the stress signal 90 and the voltage of the strain signal 92 have been scaled to the same voltage for display purposes on the oscilloscope 86 so that the peaks of the stress signal 90 and the strain signal 92 coincide in amplitude, a process sometimes referred to as "normalizing". Prior art conventional linear viscoelastic theory had assumed that the phase lag between the stress signal and the strain signal is always constant and that the strain signal always lags the stress signal as illustrated on page 12 of "Viscoelastic Properties of polymers", by John D. Ferry, published by John Wiley & Sons, Inc., 1970. Contrary to conventional linear viscoelastic theory, the present invention is based, in part, upon the discovery that under actual conditions the phase lag between the stress signal ($\sigma$) 90 and the strain signal ($\gamma$) 92 is not always constant and the strain signal ($\gamma$) 92 does not always lag the stress signal ($\sigma$) 90. Depending upon conditions in the material 4 being tested, the phase lag may vary in amount and direction.

For example, where the material 4 is a polymeric tire cord tested under conditions which simulate conditions in a running tire on a vehicle, the phase lag always varies in amount and direction. The strain signal 92 impressed upon the material 4 by the displacement generator 10 is controlled to produce as precisely sinusoidal a wave form as possible and the stress signal is allowed to vary. In most cases, under such conditions, it has been discovered that the stress signal 90 does not produce a sinusoidal wave form. The phase lag varies as a function of time.

Referring to FIG. 5 for the purpose of explaining this discovery in detail, the time interval 110 from the positive peaks 112 of the stress signal 90 and the strain signal 92 to the adjacent negative peaks 114 of the stress signal 90 and the strain 92 represents contraction of the material 4. The time interval 116 from the negative peaks 114 to the adjacent positive peaks of the stress signal 90 and the strain signal 92 represents expansion of the material 4. During the contraction time intervals 110, the strain signal 92 lags in time behind the stress signal 90, which is considered to be a positive phase lag (+δ) 118. During the expansion time interval 116 of the material 4, the stress signal (σ) 90 lags in time behind the strain signal (γ) 92, which is considered to be a negative phase lag (−δ) 120. Thus, phase lag (δ) is not constant, but varies in amount and in direction as a function of time. Phase lag approaches a minimum value at about the positive peaks 112 and at about the negative peaks 114 of the strain signal 92 and the stress signal 90. Phase lag approaches a maximum value at about the mid-point of the strain signal 92 and the stress signal 90 between their peaks 112 and 114. Thus, the phase lag changes from positive to negative and then back to positive. The negative amplitude 121a and the positive amplitude 122a of the stress signal 90 and the strain signal 92 are represented as one-half of the peak to peak distance 123a. A voltmeter, such as digital voltmeter 104 in FIG. 4, is provided to read the voltage levels corresponding to the amplitudes 121a and 122a and the peak to peak distance 123a.

Figure 6:
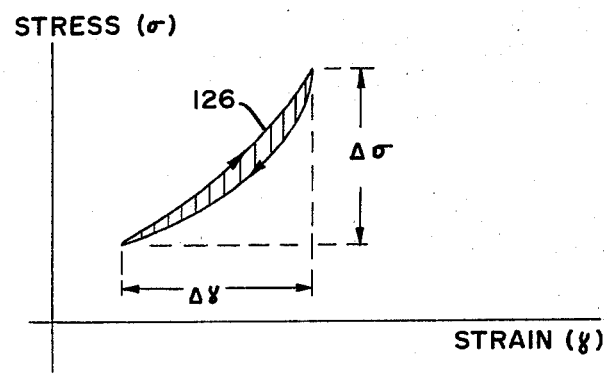
FIG. 6 is an illustration of a display of stress plotted against strain.

Referring to FIG. 6, the stress signal 90 from the first force transforming means 14 and the strain signal 92 from the second force transforming means 16 may also be displayed against one another on the oscilloscope 86, instead of being displayed in reference to time. Prior art conventional linear viscoelastic theory had assumed that when a stress signal was displayed along the vertical axis and a strain signal was displayed along the horizontal axis an elipsoid would always be formed, as illustrated on page 607, FIG. 19-1, of "Viscoelastic Properties of Polymers", by John D. Ferry, published by John Wiley & Sons, Inc., 1970. Contrary to conventional viscoelastic theory, the present invention is based, in part, upon the discovery that when a voltage proportional to the stress signal 90 is displayed along the vertical axis and a voltage proportional to the strain signal 92 is displayed along the horizontal axis, the result is a hysteresis loop 126. The area within the hysteresis loop 126 represents the energy dissipated by the material 4 during one cycle of testing, that is, the difference between the energy applied to the material 4 during expansion of the material 4 and the energy released by the material 4 during contraction. The area can be determined by photographing the hysteresis loop 126 on the oscilloscope 86. Then the area within the loop in the photograph can be determined by various techniques, such as polynominal regression or planimeter, or weighing the cut-out loops. A sequencing cam switch means 101 (FIG. 1) is provided which operates in conjunction with the speed reducer of the drive means 61. The cam switch means 101 controls and "freezes" for display the accumulation of voltage in a capacitor 105 (FIG. 4) corresponding to the area of the hysteresis loop 126. After a predetermined number of cycles of rotation of the eccentric shaft 67, the cam switch means 101 actuates a zero switch means 103 (FIG. 4) to reset the digital volt-meter 104 (FIG. 4). Means, such as the peak finder 106 and the digital volt-meter 104, are provided to measure the voltages which are proportional to the ratio of the change in the stress signal (σ) 90 to the change in the strain signal (γ) 92. This ratio is called a complex Modulus (E):

$$E = \frac{\Delta \sigma}{\Delta \gamma}$$

When the phase lag is angle dependent, the dynamic modulus (E') is defined as:

$$E' = E \cos \delta \, (\theta)$$

and the loss modulus (E'') is defined as:

$$E'' = E \sin \delta \, (\theta)$$

Temperature Chamber

Figure 9:
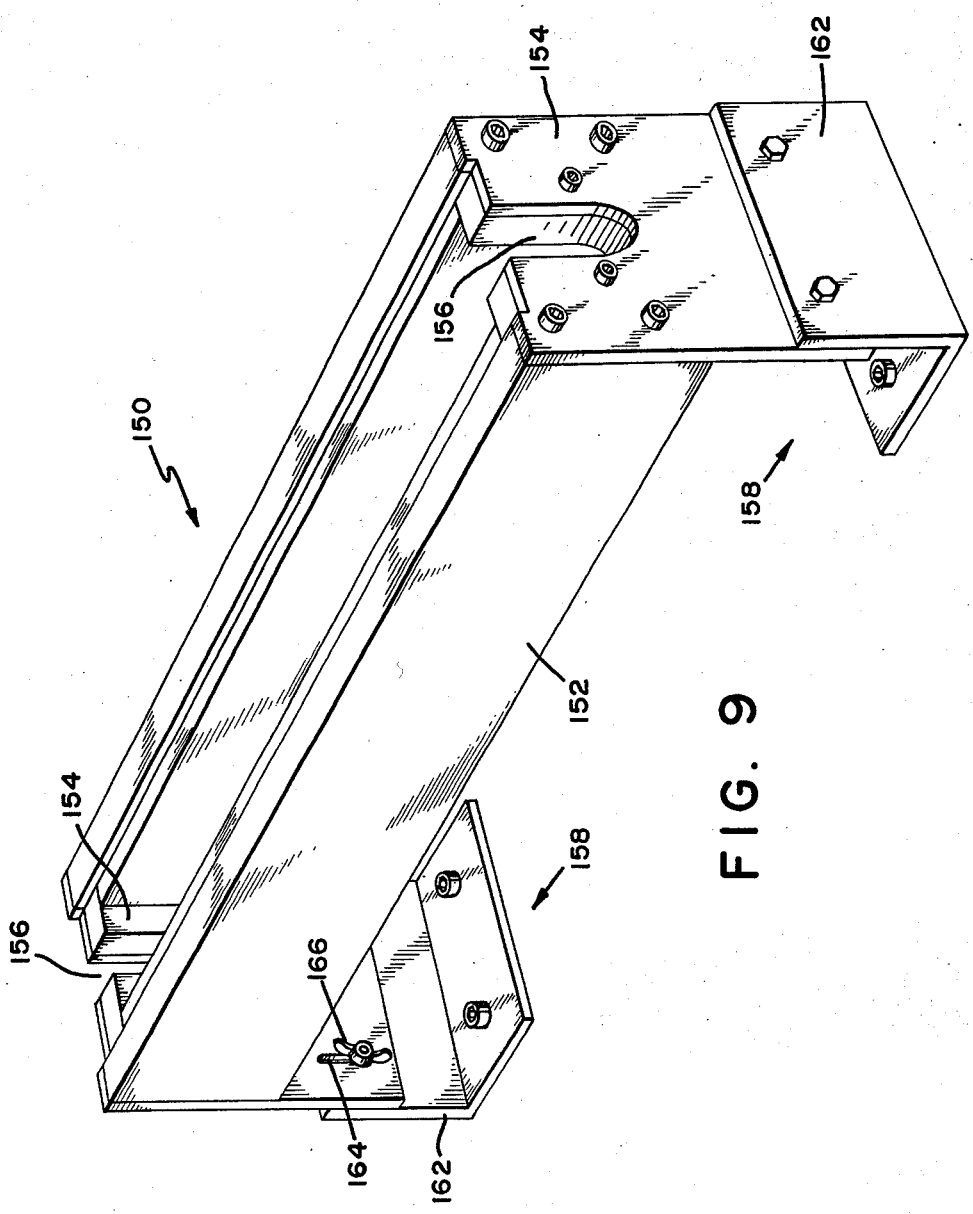
FIG. 9 is an isometric view of a portion of FIG. 1.

If it is desired to test the material 4 in the presence of heat, a temperature chamber is preferably provided. Referring to FIG. 9, the temperature chamber (referred to generally by the numeral 150) is an enclosed elongated structure having two sides 152, a bottom (not shown), and two opposed ends 154. Each of the ends 154 has a slot 156 therein. A portion of the active wire 30 extends through one of the slots 156 into the temperature chamber 150. A portion of the passive wire 32 extends through the other slot 156 at the opposite end and into the temperature chamber 150. The temperature chamber 150 also includes a cover, not shown, adapted to fit on top of the temperature chamber 150. The viscoelastic material 4 to be tested is placed into the temperature chamber 150 and the top is placed on the temperature chamber 150 thereafter. The material 4 is held in the temperature chamber 150 by the material end of the active wire 30 and the material end of the passive wire 32. The temperature chamber 150 also includes at least one thermocouple. The thermocouple senses temperature. Preferably, heat is supplied to the temperature chamber 150 by means of electrical resistors embedded in the interior of the sides 152 of the temperature chamber 150. An automatic temperature control means is provided to maintain the temperature in the temperature chamber 150 at a desired level. Thus, the temperature chamber 150 is an enclosure in which the material 4 can be conveniently inserted and removed and which is adapted to provide an environment in which the temperature may be conveniently controlled and varied as desired.

A support structure, referred to generally by the numeral 158, is provided at each end of the temperature chamber 150 for mounting the temperature chamber 150 on a platform, such as the platform 48 shown in FIG. 1. The support structure 158 includes an L-shaped bracket 162 at each end of the temperature chamber 150. Each L-shaped bracket 162 may be made in two parts, having sots 164 and wing nuts 166 to allow adjustment of the height of the temperature chamber 150.

Position Transforming Means

Referring to FIGS. 1 and 2, position transforming means 20 may be a linear variable differential transformer. The position transforming means 20 is connected to the movable member 40 of the pretension means 8. The function of the position transforming means 20 is to transform instantaneous changes in elongation of the material 4 into an electronic elongation signal.

Eccentric Mechanical Means

Referring to FIGS. 7 and 8, the eccentric means 50 includes: an eccentric adjustment means 130; an eccentric alignment means 131; and a planar adjustment means 132. The eccentric adjustment means 130 is adapted for adjustment of the displacement of the eccentric shaft 67 with reference to the center 66 (FIG. 8) of the concentric head 56. The concentric head 56 has a front planar surface 141 and a rear planar surface 143. The slot 59 is located in the front planar surface. The slot 59 has a longitudinal centerline. The eccentric slide 58 has a front planar surface 128, a rear planar surface 129 and a longitudinal centerline 133. The eccentric slide 58 is disposed in the slot 59 of the concentric head 56. The eccentric alignment means 131 is adapted for aligning the longitudinal center line 133 of the eccentric slide 58 parallel with the longitudinal center line of the slot 59 in the concentric head 56. The planar adjustment means 132 is adapted for adjusting the front planar surface 128 and the rear planar surface 129 of the eccentric slide 58 in a parallel position with reference to the front planar surface 141 and the rear planar surface 143 of the concentric head 56.

The eccentric adjustment means 130 includes an eccentric adjustment screw 134 and an adjustment bore 135 disposed in the concentric head 56 and in the eccentric slide 58 parallel to the longitudinal axis 133 of the slide 58 and the slot 59. Preferably, a longitudinal axis of the adjustment bore 135 is colinear with the longitudinal axis 133 of the slide 58. The eccentric adjustment screw 134 and the adjustment bore 135 extends from an outer circumferential edge of concentric head 56 to the adjacent, perpendicular side of the slot 59 and further extends in the adjacent, perpendicular side of the slide 58 within the slot 59. The adjustment screw 134 is disposed in the adjustment bore 135. Twisting of the screw 134 causes the eccentric slide 58 to move in the slot 59 parallel to the longitudinal centerline of the slot 59 in the concentric head 56. As a result, the eccentric adjustment screw 134 moes the eccentric shaft 67 with reference to the center 66 of the concentric head 56. Thus, the eccentric adjustment screw 134 adjusts the displacement of the eccentric shaft 67 with reference to the center 66 of the concentric head 56. Consequently, the eccentric adjustment screw 134 adjusts the amount of eccentric motion of the eccentric mechanical means 50 and the amount of displacement applied by the displacement generator 10 to the material 4 during testing.

The eccentric alignment means 131 includes a plurality of alignment screws, each in an alignment bore. The alignment screws and the alignment bores are disposed perpendicular to the longitudinal centerline 133 of the slide 58 and the longitudinal centerline of the slot 59. Preferably, the eccentric alignment means 131 includes a first alignment screw 136 in a first alignment bore, a second alignment screw 137 in a second alignment bore, and a third alignment screw 138 in a third alignment bore. The second alignment screw 137 is positioned between the first alignment screw 136 and the third alignment screw 138. Preferably, the second alignment screw 137 and the second alignment bore are positioned on a centerline of the concentric head 56 which is perpendicular to the longitudinal centerline 133 of the slide 58. Preferably, the first alignment screw 136 and the first alignment bore are positioned adjacent to one end of he eccentric slide 58. Preferably, the third alignment screw 138 and the third alignment bore are positioned adjacent to the opposite end of the eccentric slide 58. The eccentric alignment means 131 aligns the longitudinal centerline 133 of the eccentric slide 58 parallel to, but not necessarily coincident with, the longitudinal centerline of the slot 59. The eccentric slide 58 has a first longitudinal side 140 and a second longitudinal side 142. The alignment screws 136, 137 and 138 press against the first longitudinal side 140 of the eccentric slide 58. As a result, the eccentric slide 58 is pressed against the side of slot 59 adjacent to the second longitudinal side 142 of the eccentric slide 58.

Referring to FIGS. 7 and 8, the planar adjustment means 132 includes a plurality of planar screws positioned through the front planar surface 128 and the rear planar surface 129 of the eccentric slide 58. In this embodiment, four such planar adjustment screws are used, a first planar adjustment screw 144 and a second planar adjustment screw 145 at one end of the eccentric slide 58 and a third planar adjustment screw 146 and a fourth planar adjustment screw 147 at the opposing end of the eccentric slide 58. The first and fourth planar adjustment screws 144 and 147 are adjacent to the first longitudinal side 140 of the eccentric slide 58. The second and third planar adjustment screws 145 and 146 are adjacent to the second longitudinal side 142 of the eccentric slide 58. Movement of the planar adjustment screws 144, 145, 146 and 147 adjusts the front planar surface 128 and the rear planar surface 129 of the eccentric slide 58 to a parallel position with reference to the front planar surface 141 and the rear planar surface 143 of the concentric head 56.

Since the eccentric mechanical means 50 and many of its components are in rotation during operation of the apparatus 2, it is important that the components of the eccentric mechanical means 50 be positioned and held fast in precisely the desired position. If the components of the eccentric mechanical means 50 are not positioned in precisely the desired mechanical and geometric position, and held fast therein, errors in the amount of eccentricity and displacement applied to the material 4 will be introduced during testing. Such precise maintenance of position is accomplished by the eccentric adjustment means 130, the eccentric alignment means 131 and the planar adjustment means 132.

The concentric head 56 also includes an eccentric measuring device 148, such as a ruler, which measures the approximate amount of eccentricity, by measuring the displacement of the center of the eccentric shaft 67 with reference to the center 66 of the eccentric head 56 and the drive shaft 63. A more precise measurement of the amount of eccentricity is achieved by use of a conventional dial indicator.

Displacement — Eccentric Shaft

The displacement of the eccentric shaft 67 from the center of the concentric head 56 is shown more clearly in FIG. 10. After such displacement is arranged, the eccentric shaft, 67 is fixed and held fast to the concentric head 56 and both rotate together. Rotation may be either in a clockwise or in a counterclockwise direction, depending upon the direction of rotation of the drive means 61. Assume for purposes of description that the concentric head 56 and eccentric shaft 67 rotate in a counterclockwise direction, as indicated by arrow A. Reference numeral 67a designates the position of the eccentric shaft 67 when the eccentric shaft 67 is precisely colinear with the center 66 of the concentric head 56 with the first force transforming means 14 and the second force transforming means 16 and when the eccentric shaft 67 is on the side of the center 66 of the concentric head 56 adjacent to the first force transforming means 14.

When the eccentric shaft 67 rotates 90° in a counterclockwise direction from the position 67a to a position designated by numeral 67b the eccentric shaft 67 is located directly over the center 66 of he concentric head 56. When the eccentric shaft 67 again rotates 90° in a counterclockwise direction from the position 67b of the eccentric shaft 67 to a position designated by numeral 67c the eccentric shaft 67 is located on the side of center 66 of the concentric head 56 adjacent to the second force transforming means 16. Position 67c is precisely colinear with the center 66 of the eccentric head, with the first force transforming means 14 and the second force transforming means 16. Position 67c is on the opposite side of the center 66 of cencentric head 56 from position 67a. When the eccentric shaft 67 rotates 90° in a counterclockwise direction from position 67c to a position designated by numeral 67D, the eccentric shaft 67 is directly below the center 66 of the concentric head 56.

Thus, the eccentric shaft 67 rotates around the center 66 of the concentric head 56 and defines a circular path around the center 66 of the concentric head 56. The displacements 121b and 122b of the eccentric shaft 67 from the center 66 of the concentric head 56 are equal to a radius of the circular path defined by movement of the eccentric shaft 67. The displacement 121b of the eccentric shaft 67a from the center 66 of the concentric head 56 corresponds to the negative amplitude 121a shown in FIG. 5. The displcement 122b of the eccentric shaft 67c from the center 66 of the concentric head 56 corresponds to the positive amplitude 122a shown in FIG. 5. The peak-to-peak distance 123a shown in FIG. 5 is equal to twice the amplitude 122a and corresponds to twice the displacement 122b shown in FIG. 10 and to a diameter 123b of the circular path defined by the movement of the eccentric shaft 67 around the center 66 of the concentric head 56. Movement of the eccentric shaft 67 from position 67a through position 67b to position 67c causes expansion of the material 4 and corresponds to the time interval 116 shown in FIG. 5. Movement of the eccentric shaft 67 from position 67c through position 67d to position 67a produces contraction of the material 4 and corresponds to the time interval 110 in FIG. 5.

The displacement generator 10 is capable of providing a displacement 121b or 122b on the order of approximately ± 2.5 millimeters. A large portion of this displacement is absorbed by the material 4 and the strain spring 70. As a result, the displacement felt by the first force transforming means 14 and the second force transforming means 16 is reduced to a displacement on the order of 0.12 millimeters.

Micrometer Means

Figure 11:
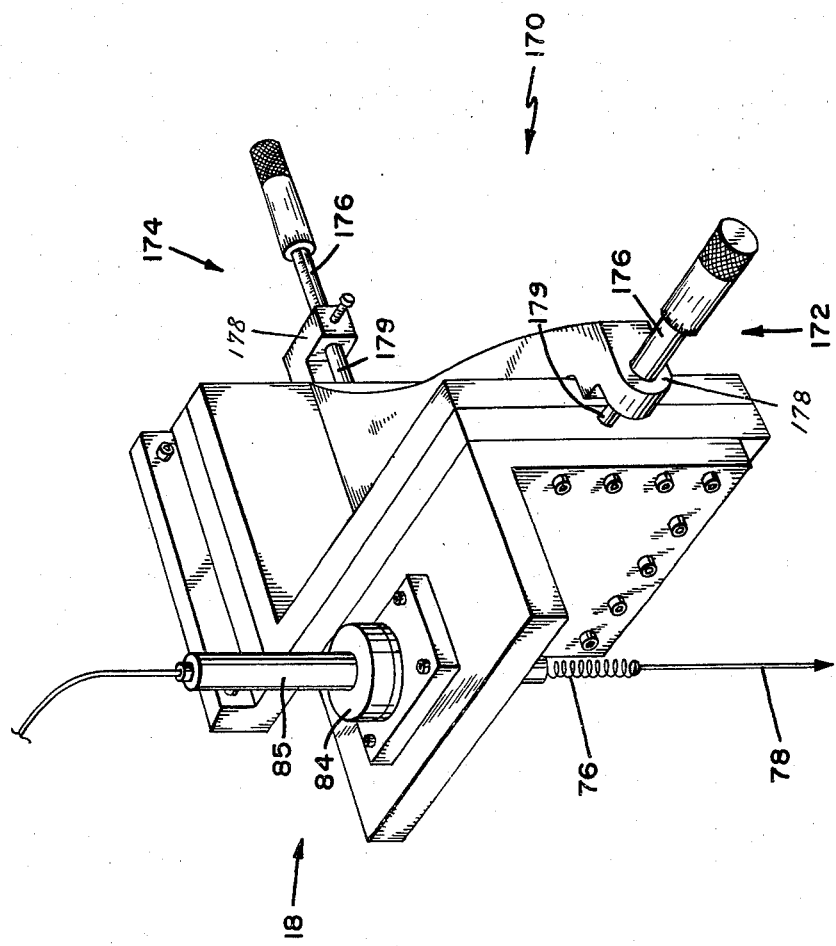
FIG. 11 is an isometric view of a portion of FIG. 1.

Referring to FIG. 11, the third force transforming means 18 is mounted on a first micrometer means 170. The first micrometer means 170 has a first adjustment means 172 and a second adjustment means 174. Each of the adjustment means 172 and 174 uses an accurately machined screw 176 threaded in a sleeve 178 and a spindle 179 located at the forward end of the screw 176. The screw 176 of the first adjustment means 172 is arranged at right angles to the screw 176 of the second adjustment means 174. As a result, the first micrometer means 170 is capable of adjusting the position of the third force transforming means 18 in two planes, one plane perpendicular to the other plane. Referring to FIG. 3, the first micrometer means 170 of FIG. 11 is capable of adjusting the third force transforming means 18, the differentiating spring 76 and the differentiating wire 78 so that they are precisely perpendicular to the line formed by the first force transforming means 14, the center 66 of the eccentric head 56 and the second force transforming means 16.

The second force transforming means 16 is mounted on a second micrometer means (not shown) which is similar to the micrometer means shown in FIG. 11. The second micrometer means, upon which the second force transforming means 16 is mounted, is used to adjust the position of the second force transforming means 16 so that the second force transforming means 16, the strain spring 70 and the strain wire 72 are colinear with the center of the eccentric head 56.

Optionally, the first force transforming means 14 may also be mounted on a third micrometer means (not shown) which is similar to the first micrometer means shown in FIG. 11. The third micrometer means, upon which the first force transforming means 14 is optionally mounted, may be mounted in turn on the movable member 40 of the pretension means 8. The third micrometer means, upon which the first force transforming means 14 is optionally mounted, is used to position and align the first force transforming means 14 so that it is colinear with the passive wire 32, the active wire 30, and the center 66 of the eccentric head 56; and also so that the first force transforming means 14 is colinear with the second force transforming means 16.

Tension, Shear, Compression

Figure 12:
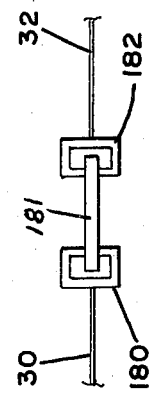
FIG. 12 is a simplified illustration of a second embodiment of a holding means used for testing and measuring a material's ability to withstand fatigue.

Referring to FIG. 12, in a second embodiment, a material 181, such as rubber, is to be tested to determine and measure its ability to withstand fatigue, that is, its ability to endure cyclic tension and its hysteresis characteristics. The holding means 6 may use a first clamp 180 and a second clamp 182 to hold the material 181, instead of the hooks 34 and 36, shown in FIG. 1. The first clamp 180 is connected to the active wire 30 and the second clamp 182 is connected to the passive wire 32.

Figure 13:
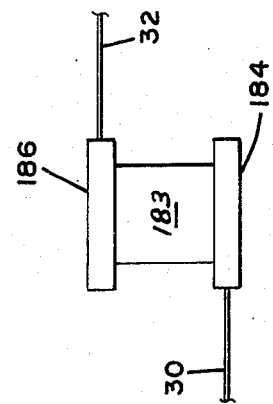
FIG. 13 is a simplified illustration of a third embodiment of a holding means used for testing and measuring a material's ability to withstand shearing forces.

Referring to FIG. 13, in a third embodiment, a material 183 is to be tested for shear. The material 183 may be held by a first shear plate 184 and a second shear plate 186, instead of the hooks 34 and 36, shown in FIG. 1, to hold the material 4. The first shear plate 184 is connected to the active wire 30 and the second shear plate 186 is connected to the passive wire 32. Depending on the type of shear applied, the active wire 30 and the passive wire 32 may be replaced by rigid rods.

Referring to FIG. 14, in a fourth embodiment, a material 187 is to be tested for compression. The material 187 is arranged between a first compression plate 188 and a second compression plate 190, one plate being at each end of the material 187, instead of the hooks 34 and 36, shown in FIG. 1. The first compression plate 188 is connected to an active rod 194 and the second compression plate 190 is connected to a passive rod 196. Both rods 194 and 196 are rigid. Such rods 194 and 196 may be used to replace the active wire 30 and the passive wire 32 in FIG. 13 for shear.

Referring to FIG. 15, for testing and measurement of compression, the active wire 30 is connected to the centerpiece 60 by a member having a circular mounting means 192, instead of the stress arm 69 shown in FIG. 3. The mounting means 192 is attached to the centerpiece 60 at various points around the circumference of the centerpiece 60 and the mounting means 192. Optionally, the mounting means 192 may be used for testing and measurement of material 4 in reference to stress, strain and fatigue, as well.

Method

Referring to FIG. 1, the present invention also includes a method for testing a viscoelastic solid, such as the material 4 and measuring selected properties of the material 4. The method includes the following steps: applying strain to the material 4, with resulting stress also being developed in the material 4 when such strain is applied to the material 4; transforming the strain applied to the material 4 into an electrical strain signal ($\gamma$) 92 having a strain wave form and an amplitude; transforming the resulting stress into an electrical stress signal ($\sigma$) 90 having a stress wave form and an amplitude; controlling the strain applied to the material 4 to produce at least a substantially sinusoidal strain wave form representing strain and preferably a strain wave form which is as precisely sinusoidal as possible; and allowing the stress applied to the material to produce a stress wave form representing stress which may be non-sinusoidal or which may be sinusoidal.

The method further includes observing that there is a phase lag between the strain wave form and the stress wave form and that the phase lag varies in amount and sometimes in direction, depending upon the characteristics of the material. It has been found for certain selected polymeric tire cord material that the phase lag varies both in amount and in direction, as illustrated in FIG. 5. On the other hand, it has been found for certain types of rubber that the phase lag appears to vary only in amount, but possibly not in direction.

Referring to FIG. 5, the step of observing that the phase lag varies in amount and sometimes in direction includes: displaying the strain wave form and the stress wave form as a function of time on the same scale; and arranging the amplitudes of the strain wave form and the stress wave form to be equal, such as by a process known as "normalization."

Referring to FIG. 6, the method further includes: displaying the stress wave form along a vertical axis; displaying the strain wave form along a horizonal axis, without normalization; observing a formation of a hysteresis loop 26; and determining the area within the hysteresis loop. The area within the hysteresis loop reflects the energy loss, that is, the difference between the energy applied to the material 4 during expansion and the energy released by the material 4 during contraction.

Referring to FIG. 4, the step of measuring the area within the hysteresis loop may include: using an integrating means 28 to measure such area. The step of using an integrating means includes: transforming the strain applied to the material 4 into a differentiated strain signal 94; and integrating the differentiated strain signal 94 and the stress signal 90. The step of transforming the strain applied to the material 4 into a differentiated strain signal includes: differentiating the strain mechanically by the previously described arrangement of the differentiating mounting means 73 at an angle of 90° in reference to the strain mounting means 64.

The method for using the apparatus 2 of the present invention includes the following procedure. Initially, the apparatus 2 is prepared for use by the following steps. First, if necessary, align the apparatus 2 so that the stress arm 69 is arranged colinearly with the strain arm 71, by arranging the stress mounting means 75 at an angle of approximately and preferably precisely 180° with respect to the strain mounting means 64 and arranging the differentiating mounting means 73 at an angle of 90° with respect to the stress mounting means 75 and with respect to the strain mounting means 64. Second, if necessary, calibrate the voltage levels of the first force transforming means 14, the second force transforming means 16 and the third force transforming means 18 so that their voltage levels can be converted to physical units. Third, set the amount of strain to be applied to the material 4 at a desired level by adjusting the offset of the eccentric shaft 67 of the eccentric slide 58 with respect to the center 66 of the eccentric head 56.

After the foregoing preparation, the method further includes following steps. Fourth, place a test spring (not shown) in the holding means 6 in the same position in which the material 4 will subsequently be placed for testing. Using such a test spring, set the pretension means 8 to apply a desired level by adjusting the movable member 40. The desired level of pretension corresponds to a median level of stress applied to the material 4. The median level of stress is represented in FIG. 5 by the horizontal axis along which time and angle are displayed. The horizontal axis in FIG. 5 is midway between the positive peaks 112 and negative peak 114 of the stress signal 90 and the strain signal 92. Fifth, establish a zero integral strain point. This is accomplished while the test spring is in the position where the material 4 will subsequently be placed for testing in the holding means 6. The differentiated strain output level from the third force transforming means 18 (arranged at a 90° angle) is adjusted so that the integral output from the integrating means is zero. Sixth, remove the test spring and replace it with the material 4 to be tested. Seventh, if the material is to be subjected to heat, set the desired temperature under which the material 4 is to be tested by means of the temperature chamber 150. Eighth, bring the material 4 back to the same desired pretension level as was previously set when the test spring was used in the holding means 6. Ninth, set the pretension control, including the servo motor 44 to apply the desired pretension to the material 4. Tenth, allow the material 4 to reach an equilibrium condition after the application of heat and pretension.

Eleventh, if desired, photograph the hysteresis loop on the display means. Twelfth, if desired, photograph the wave forms of the stress signal and the strain signal on the display means. Thirteenth, if desired, read the integral energy loss from the voltmeter 104 (FIG. 4) or from a display means, such as the oscilloscope 86. Fourteenth, if desired, read the voltage corresponding to the peak to peak distance 123a in FIG. 5 and the strain to stress ratio represented in FIG. 6 to ascertain the complex modulus E.

We claim:

1. An apparatus for testing a viscoelastic material, comprising:
   a holding means connected to the material for holding the material in a predetermined position during testing;
   a pretension means coupled to the material for applying tension to the material during testing;
   a displacement generator having an eccentric means coupled to the material for applying cyclic displacement to the material; and
   a mechanical-electrical transforming means coupled to the material for transforming mechanical motion into electrical signals.

2. The apparatus for testing a viscoelastic material according to claim 1 wherein said mechanical-electrical transforming means comprises:
   a first force transforming means for transforming mechanical stress developed in the material into an electrical stress signal; and
   a second force transforming means for transforming mechanical strain applied to the material into an electrical strain signal.

3. The apparatus for testing a viscoelastic material according to claim 2 and further comprising a differentiating means for differentiating the strain signal from the second force transforming device to produce a differentiated strain signal.

4. The apparatus for testing a viscoelastic material according to claim 2 wherein said strain signal has at least a substantially sinusoidal wave form; and there is a phase lag between said stress signal and said strain signal which may vary in amount and direction as a function of time.

5. The apparatus for testing viscoelastic material according to claim 1 wherein said mechanical-electrical transforming means comprises:
   a first force transforming means for transforming mechanical stress applied to the material into an electrical stress signal; and
   a third force transforming means for transforming mechanical strain applied to the material into an electrical cosine signal.

6. The apparatus for testing of the viscoelastic material according to claim 1 and further comprising a position transforming means connected to said pretension means for transforming instantaneous elongation in the material into an electrical signal.

7. The apparatus for testing a viscoelastic material according to claim 1 and further comprising: an integrating means for integration of a stress-strain hysteresis loop; and a display means for displaying an output of the integrating means to measure the area of the hysteresis loop and thereby determine energy loss.

8. The apparatus for testing viscoelastic material according to claim 1 and further comprising a temperature chamber for controlling the temperature of the environment in which the material is held during testing.

9. The apparatus for testing a viscoelastic material according to claim 1 wherein said eccentric means comprises:
   a drive means which is a source of rotating power to the eccentric means;
   a rotatably concentric head driven by said drive means and having a center;
   an eccentric slide mounted on said concentric head for rotation therewith, said eccentric slide having an eccentric shaft, said eccentric slide movable with reference to said concentric head for eccentric displacement of said eccentric shaft with reference to said center of said concentric head; and
   a centerpiece mounted on said eccentric shaft and coupled to the material for transmitting cyclic displacement to said material, said eccentric shaft rotatable with reference to said centerpiece.

10. The apparatus for testing viscoelastic material according to claim 9 wherein said eccentric means further comprises:
    an eccentric adjustment means for adjustment of said displacement of said eccentric shaft with reference to said center of said concentric head; said concentric head having a front planar surface and a slot in said front planar surface; said slot having a longitudinal centerline; said eccentric slide having a front planar surface and a longitudinal centerline, said eccentric slide disposed in said slot of said concentric head;
    an eccentric alignment means for aligning said longitudinal centerline of said eccentric slide with reference to said longitudinal centerline of said slot in said concentric head; and
    a planar adjustment means for adjusting said front planar surface of said eccentric slide in a parallel position with reference to said front planar surface of said concentric head.

11. The apparatus for testing a viscoelastic material according to claim 9 wherein said centerpiece comprises:
    a strain mounting means on said centerpiece and coupled to said material;
    a stress mounting means on said centerpiece and coupled to said material; and
    a differentiating mounting means on said centerpiece and coupled to said material; and wherein
    said stress arm is arranged at an angle of 90° with respect to said differentiating mounting means;
    said stress arm is arranged at an angle of 180° with respect to said strain mounting means;
    said differentiating mounting means is arranged at an angle of 90° with respect to said stress arm and with respect to said strain mounting means.

12. An apparatus for testing a viscoelastic material to determine the physical-structural properties of the material comprising:
    a holding means connected to the material for holding the material in a predetermined position during testing;
    a pretension means coupled to the material for applying tension to the material during testing;
    a displacement generator having an eccentric means coupled to the material for applying cyclic displacement to the material;

a first force transforming means for transforming mechanical stress applied to the material into an electrical stress signal;

a second force transforming means for transforming mechanical strain applied to the material into an electrical strain signal; and a third force transforming means arranged at an angle of 90° with reference to said first force transforming device and with reference to said second force transforming device for transforming mechanical strain applied to the material into an electrical differentiated strain signal.

13. The apparatus for testing a viscoelastic material according to claim 12 wherein said strain signal has at least a substantially sinusoidal wave form; and there is a phase lag between said stress signal and said strain signal, which may vary in amount and direction as a function of time.

14. The apparatus for testing of the viscoelastic material according to claim 12 and further comprising a position transforming means connected to said pretension means for transforming instantaneous elongation in the material into an electrical signal.

15. The apparatus for testing a viscoelastic material according to claim 12 and further comprising: an integrating means for integration of a stress-strain hysteresis loop; and a display means for displaying an output of the integrating means to measure the area of the hysteresis loop and thereby determine energy loss.

16. The apparatus for testing viscoelastic material according to claim 12 and further comprising a temperature chamber for controlling the temperature of the environment in which the material is held during testing.

17. The apparatus for testing a viscoelastic material according to claim 12 wherein said eccentric means comprise:

a drive means which is a source of rotating power to the eccentric mechanical means;

a rotatably concentric head driven by said drive means and having a center;

an eccentric slide mounted on said eccentric head for rotation therewith, said eccentric slide having an eccentric shaft, said eccentric slide movable with reference to said concentric head for eccentric displacement of said eccentric shaft from said center of said concentric head; and a centerpiece mounted on said eccentric shaft and coupled to the material for transmitting cyclic displacement of said material, said eccentric shaft rotatable with reference to said centerpiece.

18. The apparatus for testing viscoelastic material according to claim 17 wherein said eccentric means further comprises:

an eccentric adjustment means for adjustment of said displacement of said eccentric shaft with reference to said center of said concentric head; said concentric head having a front planar surface and a slot in said front planar surface; said slot having a longitudinal centerline; said eccentric slide having a front planar surface and a longitudinal centerline, said eccentric slide disposed in said slot of said concentric head;

an eccentric alignment means for aligning said longitudinal centerline of said eccentric slide with reference to said longitudinal centerline of said slot in said concentric head; and a planar adjustment means for adjusting said front planar surface of said eccentric slide in a parallel position with reference to said front planar surface of said concentric head.

19. A method for testing a viscoelastic material and measuring selected properties comprising:

applying strain to the material, with resulting stress also applied to the material;

transforming said strain applied to the material into an electrical strain signal having a strain wave form and an amplitude;

transforming said resulting stress applied to the material into an electrical stress signal having a stress wave form and an amplitude;

controlling said strain applied to the material to produce at least a substantially sinusoidal strain wave form representing strain; and allowing said stress to vary to produce a stress wave form representing stress.

20. The method for testing viscoelastic material and measuring selected properties according to claim 19 and further comprising:

observing that there is a phase lag between the strain wave form and the stress wave form and that the phase lag varies in amount and sometimes in direction, depending upon the characteristics of the material.

21. The method for testing a viscoelastic material and measuring selected properties according to claim 19 and further comprising:

displaying the strain wave form and the stress wave form as a function of time on the same scale; and arranging the amplitudes of the strain wave form and the stress wave form to be equal, thereby allowing observation of a phase lag between the strain wave form and the stress wave form, the phase lag varying in amount and sometimes in direction, depending upon the characteristics of the material.

22. The method for testing a viscoelastic material and measuring selected properties according to claim 19 and further comprising:

displaying the stress wave form along a vertical axis;

displaying the strain wave form along a horizontal axis;

observing a formation of a hysteresis loop; and determining the area of the hysteresis loop, said area indicating energy loss in the material.

23. The method for testing viscoelastic material and measuring selected properties according to claim 22 wherein said step of determining the area of the hysteresis loop comprises:

transforming said strain applied to the material into a differentiated strain signal; and integrating said differentiated strain signal and said stress signal.

24. The method for testing viscoelastic material and measuring selected properties according to claim 23 wherein said step of transforming said strain applied to the material into a differentiated strain signal comprises differentiating said strain signal mechanically.

25. An apparatus for testing a viscoelastic material to determine the physical-structural properties of the material comprising:

a holding means connected to the material for holding the material in a predetermined position during testing;

a pretension means coupled to the material for applying tension to the material during testing;

a displacement generator having an eccentric means coupled to the material for applying cyclic displacement to the material;

a first force transforming means for transforming mechanical stress applied to the material into an electrical stress signal;

a second force transforming means for transforming mechanical strain applied to the material into an electrical strain signal;

a third force transforming means arranged at an angle of 90° with reference to said first force transforming device and with reference to said second force transforming device for transforming mechanical strain applied to the material into an electrical differentiated strain signal;

a position transforming means connected to said pretension means for transforming instantaneous elongation in the material into an electrical signal;

an integrating means for integration of a stress-strain hysteresis loop;

a display means for displaying an output of the integrating means to measure the area of the hysteresis loop and thereby determine energy loss; and a temperature chamber for controlling the temperature of the environment in which the material is held during testing; wherein:

said strain signal has at least a substantially sinusoidal wave form; and there is a phase lag between said stress signal and said strain signal, which may vary in amount and direction as a function of time;

said eccentric means comprise:

a drive means which is a source of rotating power to the eccentric mechanical means;

a rotatably concentric head driven by said drive means and having a center;

an eccentric slide mounted on said concentric head for rotation therewith, said eccentric slide having an eccentric shaft, said eccentric slide movable with reference to said concentric head for eccentric displacement of said eccentric shaft from said center of concentric head;

a centerpiece mounted on said eccentric shaft and coupled to the material for transmitting cyclic displacement of said material, said eccentric shaft rotatable with reference to said centerpiece;

an eccentric adjustment means for adjustment of said displacement of said eccentric shaft with reference to said center of said concentric head; said concentric head having a front planar surface and a slot in said front planar surface; said slot having a longitudinal centerline; said eccentric slide having a front planar surface and a longitudinal centerline, said eccentric slide disposed in said slot of said concentric head;

an eccentric alignment mean for aligning said longitudinal centerline of said eccentric slide with reference to said longitudinal centerline of said slot in said concentric head; and a planar adjustment means for adjusting said front planar surface of said eccentric slide in a parallel position with reference to said front planar surface of said concentric head.

26. A method for testing a viscoelastic material and measuring selected properties comprising:

applying strain to the material, with resulting stress also applied to the material;

transforming said strain applied to the material into an electrical strain signal having a strain wave form and an amplitude;

transforming said resulting stress applied to the material into an electrical stress signal having a stress wave form and an amplitude;

controlling said strain applied to the material to produce at least a substantially sinusoidal strain wave form representing strain;

allowing said stress to vary to produce a stress wave form representing stress;

displaying the strain wave form and the stress wave form as a function of time on the same scale;

arranging the amplitudes of the strain wave form and the stress wave form to be equal, thereby allowing observation of a phase lag between the strain wave form and the stress wave form, the phase lag varying in amount and sometimes in direction, depending upon the characteristics of the material;

displaying the stress wave form along a vertical axis;

displaying the strain wave form along a horizontal axis, said stress wave form and said strain wave form thereby forming a hysteresis loop;

transforming said strain applied to the material into a differentiated strain signal by differentiating said strain signal mechanically; and integrating said differentiated strain signal and said stress signal to determine the area of the hysteresis loop, said area indicating energy loss in the material.

* * * * *

Disclaimer 3,969,930.—*Dusan Ciril Prevorsek*, *Young Doo Kwon* and *Raj Kumar Sharma*, Morristown, and *Edward T. Gilliam*, Lake Hiawatha, N.J. TESTING VISCOELASTIC SOLIDS. Patent dated July 20, 1976. Disclaimer filed Mar. 13, 1980, by the assignee, *Allied Chemical Corporation*.

Hereby enters this disclaimer to claims 1, 2, 4, 6, 8 and 19–22 of said patent.

[*Official Gazette July 22, 1980.*]